(12) United States Patent
Na

(10) Patent No.: US 7,810,893 B2
(45) Date of Patent: Oct. 12, 2010

(54) APPARATUS FOR REGULATING VISCOSITY OF INK

(76) Inventor: Jong-Kap Na, 215-702, Olympic Seonsuchon Apt., Oryun-dong, Songpa-gu, Seoul, 138-787 (KR)

( * ) Notice: Subject to any disclaimer, the term of this patent is extended or adjusted under 35 U.S.C. 154(b) by 848 days.

(21) Appl. No.: 11/575,714

(22) PCT Filed: Sep. 30, 2005

(86) PCT No.: PCT/KR2005/003256

§ 371 (c)(1), (2), (4) Date: Mar. 21, 2007

(87) PCT Pub. No.: WO2006/080673

PCT Pub. Date: Aug. 3, 2006

(65) Prior Publication Data

US 2008/0062212 A1    Mar. 13, 2008

(30) Foreign Application Priority Data

Sep. 30, 2004 (KR) .................... 10-2004-0078120
Jun. 21, 2005 (KR) .................... 10-2005-0053443

(51) Int. Cl.
*B41J 2/195* (2006.01)
(52) U.S. Cl. .......................................... 347/6
(58) Field of Classification Search ........... None
See application file for complete search history.

(56) References Cited

U.S. PATENT DOCUMENTS

| 4,568,953 A | * | 2/1986 | Aoki et al. ............... 347/65 |
| 5,502,467 A | | 3/1996 | Hoisington et al. |
| 2003/0080644 A1 | * | 5/2003 | Nelson et al. ............. 310/196 |

FOREIGN PATENT DOCUMENTS

| FR | 2801382 | 5/2001 |
| GB | 2360741 | 10/2001 |

OTHER PUBLICATIONS

Search Report issued in International Patent Application No. PCT/KR2005/003256 on Jan. 6, 2006.

\* cited by examiner

*Primary Examiner*—Stephen D Meier
*Assistant Examiner*—Alexander C Witkowski
(74) *Attorney, Agent, or Firm*—Stein McEwen, LLP

(57) ABSTRACT

Disclosed is an apparatus for regulating viscosity of ink, which is installed on a flow path of ink in a printing device for regulation of ink viscosity. The apparatus includes a housing installed on the flow path and having an introduction hole and a discharge hole through which ink is introduced and discharged; a rotary shaft installed in the housing and to which at least one rotating fan is coupled to rotate along with flow of the ink; a sensed member having a sensed body at one end thereof and coupled to the rotary shaft to rotate together with the rotary shaft; and a sensor for sensing the sensed body.

4 Claims, 7 Drawing Sheets

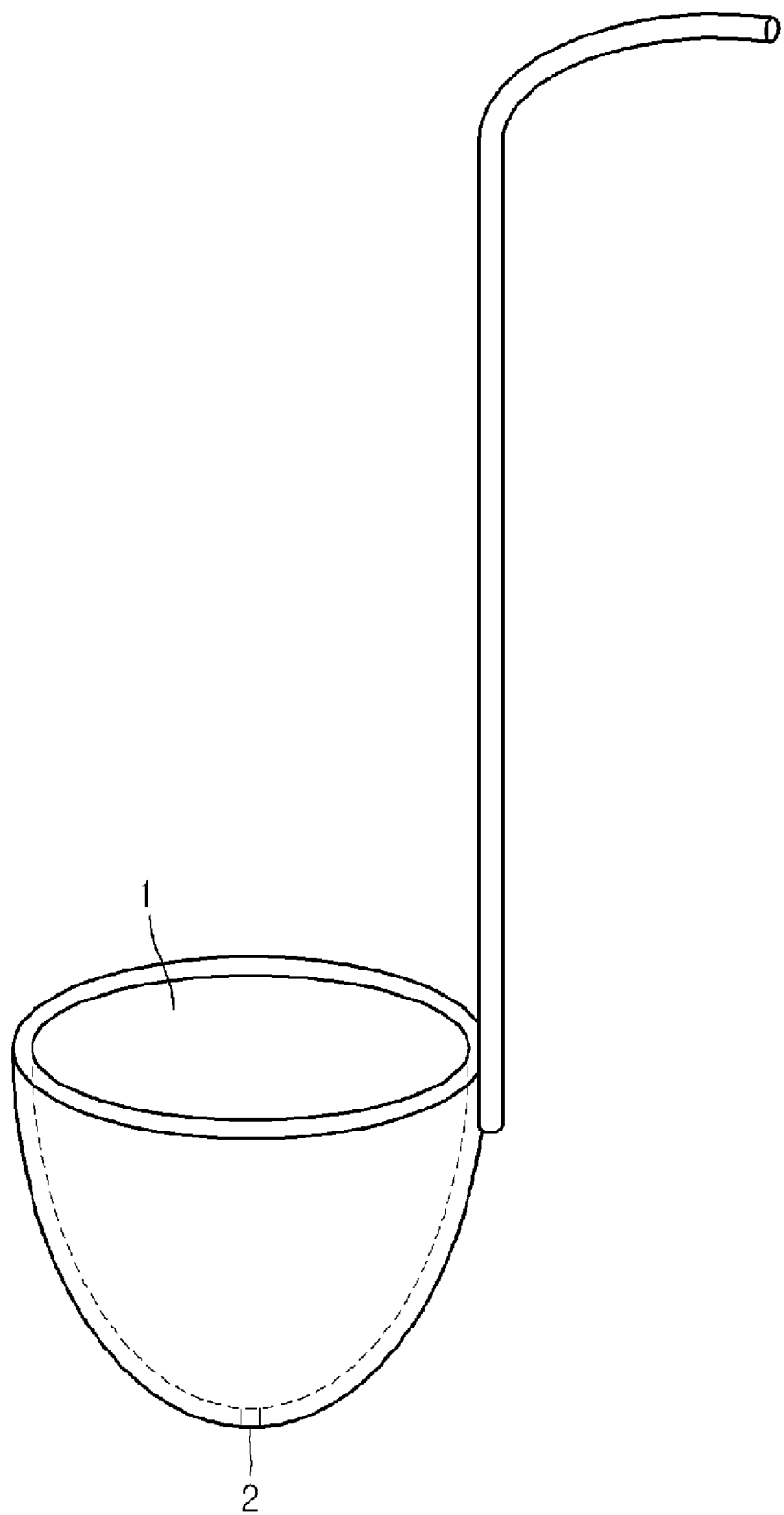
[Fig. 1]

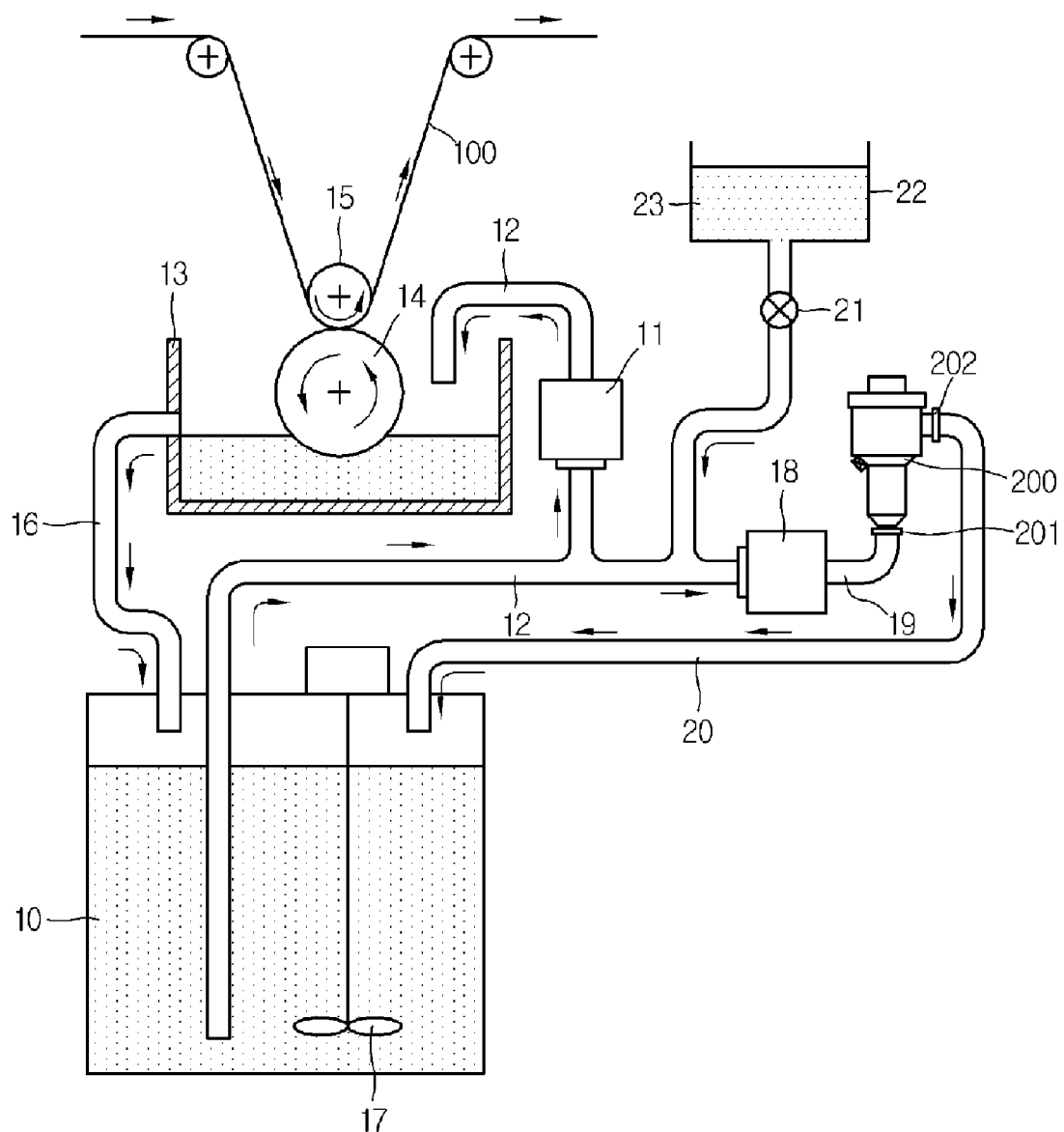
[Fig. 2]

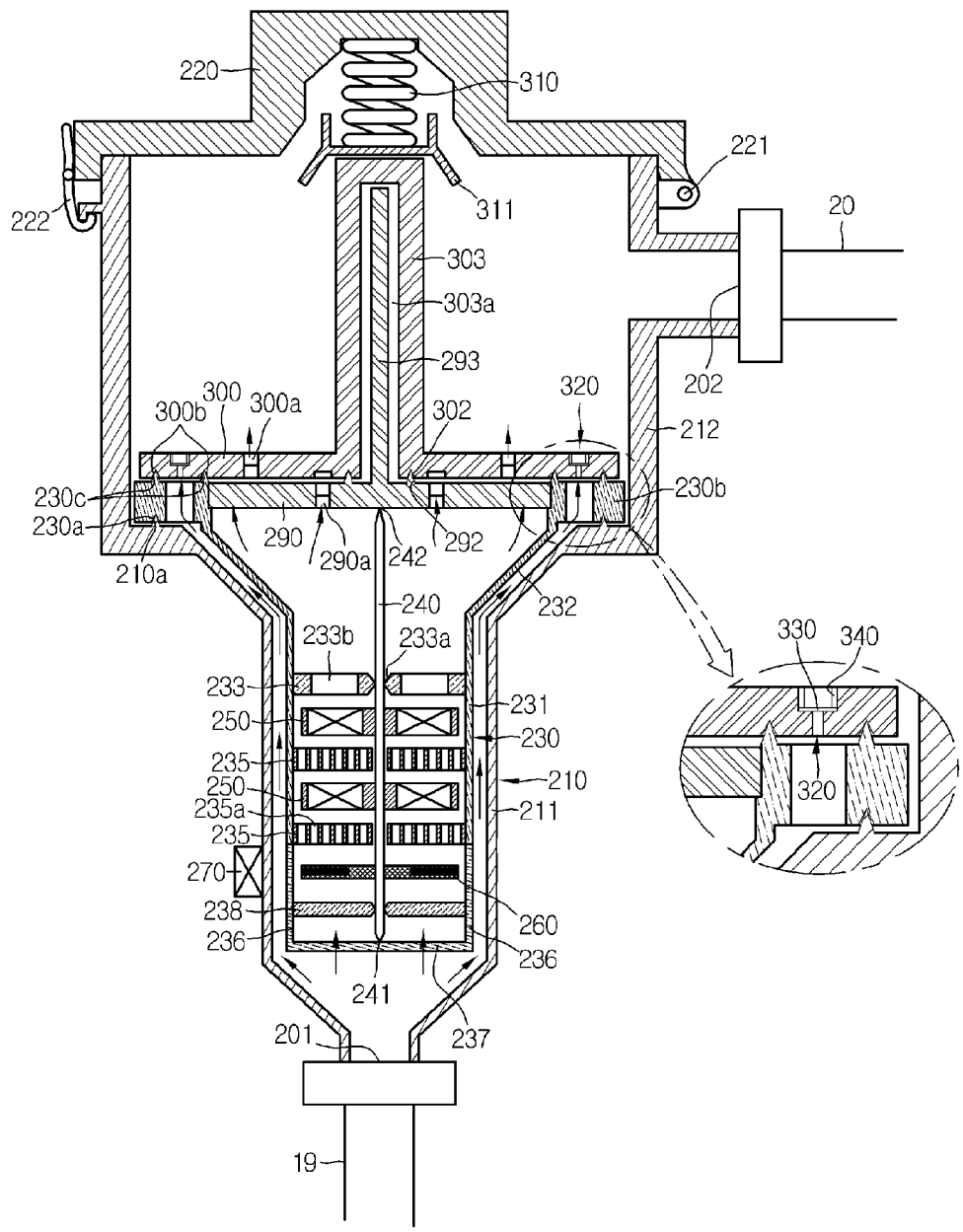
[Fig. 3]
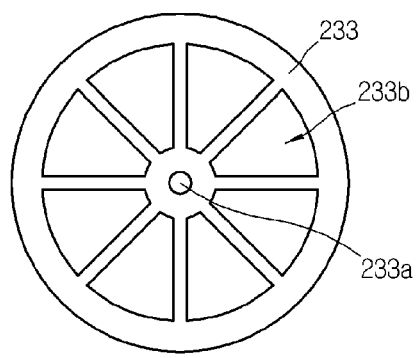
[Fig. 4]

[Fig. 5]
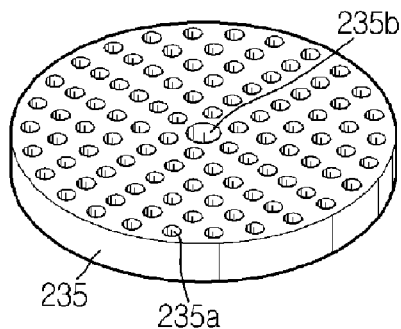
[Fig. 6]
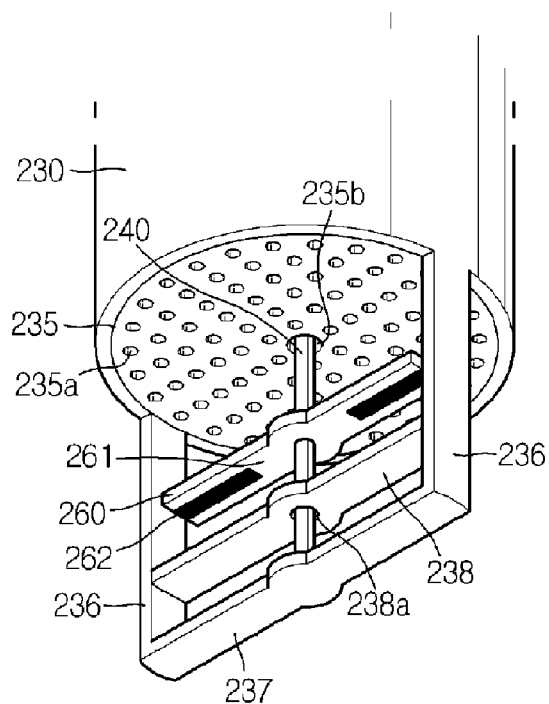
[Fig. 7]
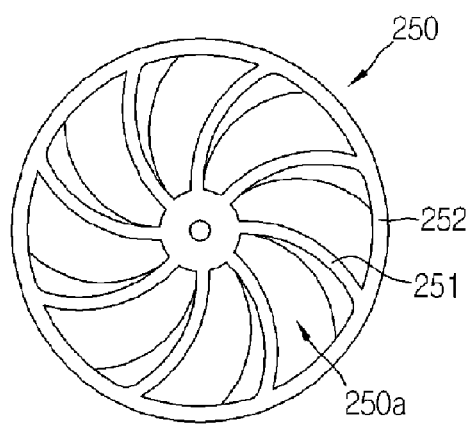

[Fig. 8]
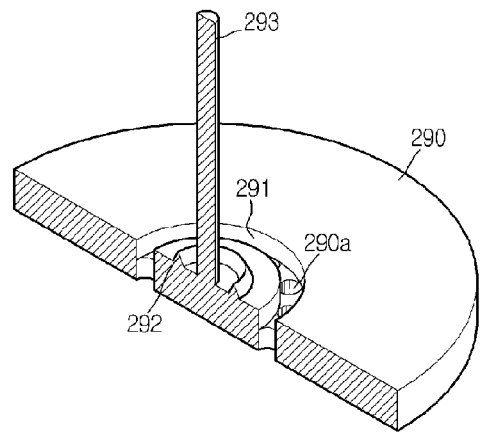
[Fig. 9]
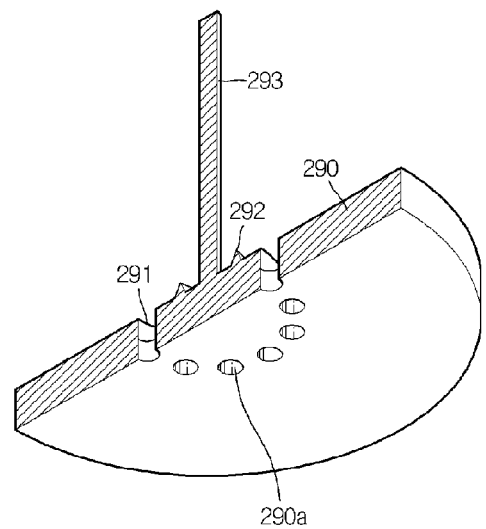
[Fig. 10]
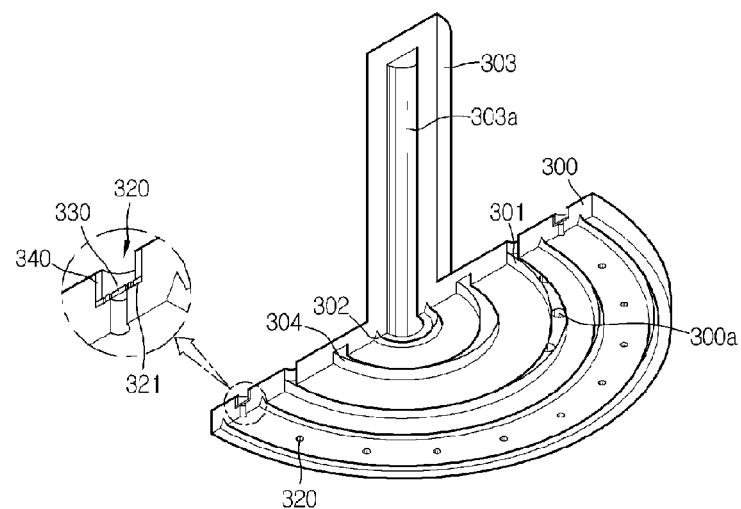

[Fig. 11]
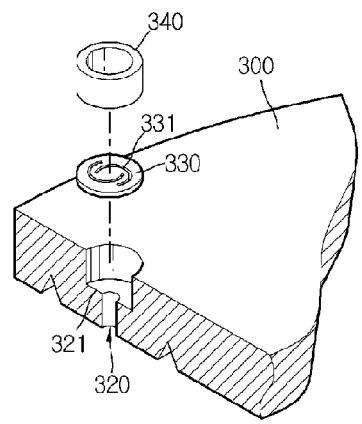
[Fig. 12]
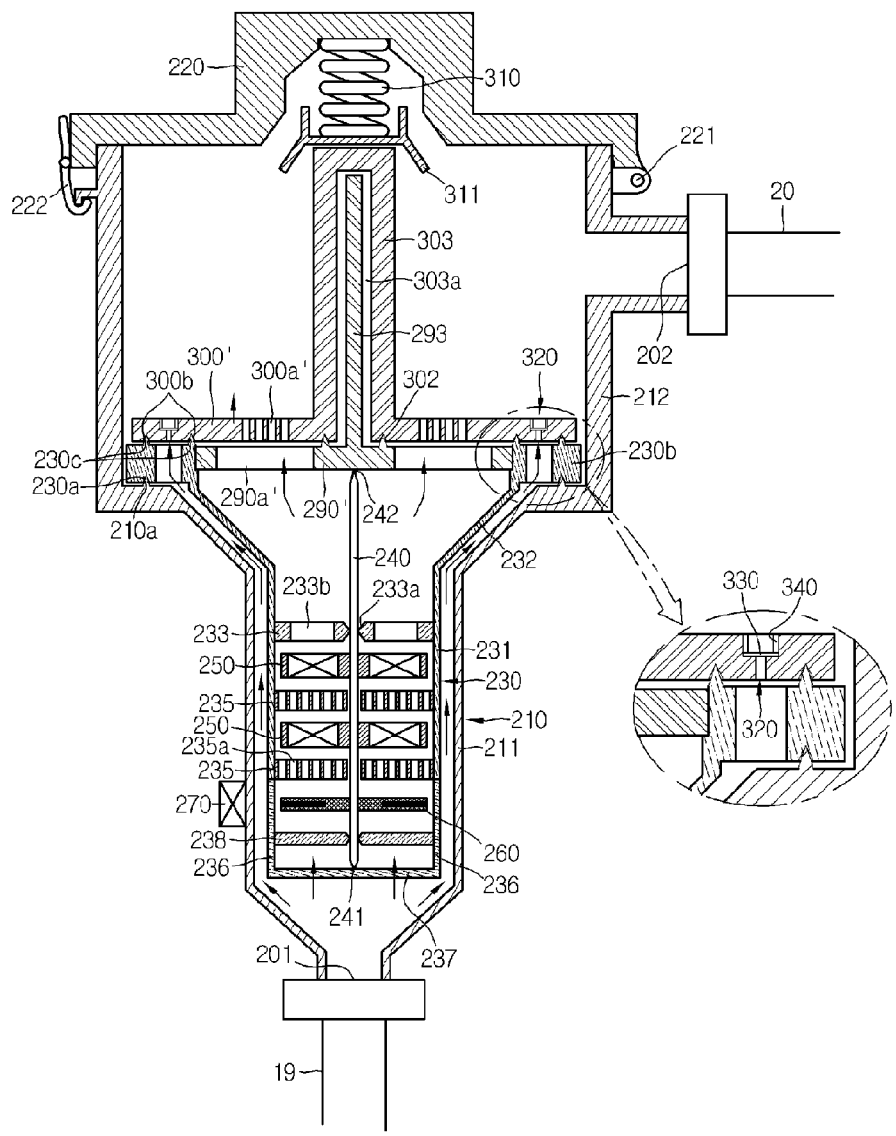

[Fig. 13]
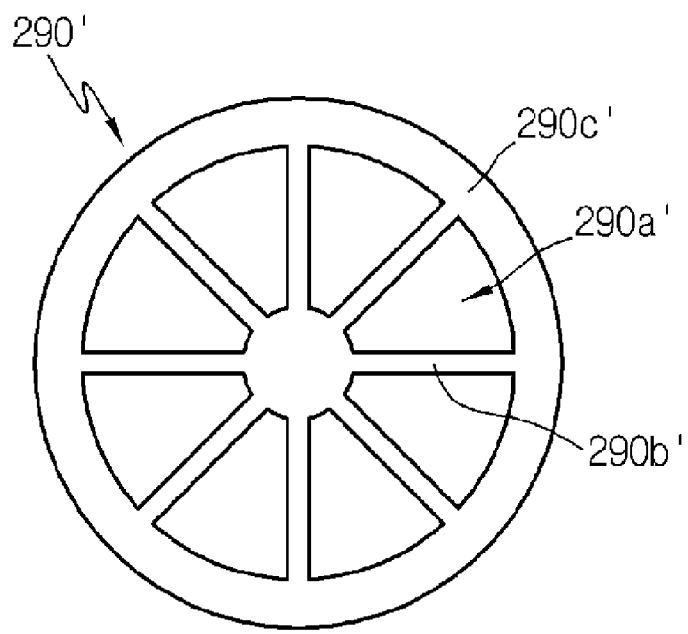
[Fig. 14]
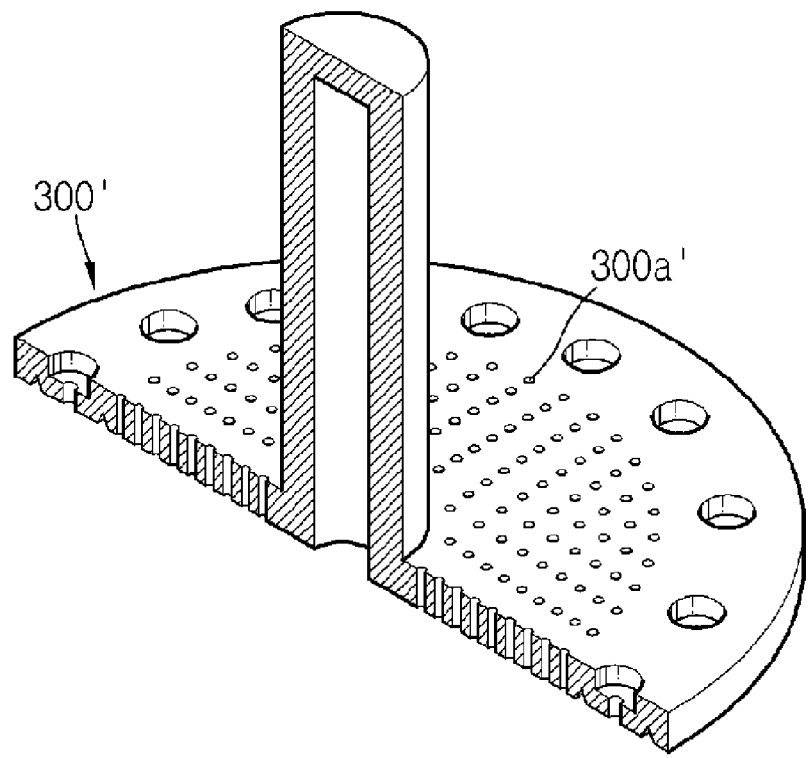

APPARATUS FOR REGULATING VISCOSITY OF INK

TECHNICAL FIELD

The present invention relates to an apparatus for regulating viscosity of ink, and more particularly to an apparatus for regulating viscosity of ink used in a printing device within a predetermined range.

BACKGROUND ART

Viscosity of ink is very important to a printing device that prints a large amount of printed matters. Since ink contains volatile solution in itself, its concentration tends to become higher as time goes. If viscosity of ink is changed as mentioned above, improvement of ink quality is not expected and a flow path in the printing device may be clogged due to the ink, causing malfunction of the device. Thus, most printing devices need a means for suitably keeping viscosity of ink within a predetermined range.

One of conventional ink viscosity measuring methods is depending much on a manual work as shown in FIG. 1. That is to say, after ink is filled in a container 1 having a hole 2 of a certain size at its bottom, a time that the ink completely gets out of the container 1 through the hole 2 is measured to calculate viscosity of ink. However, this method requires too much time for measurement, and cannot ensure accurate measurement since the measurement should be continued for the last drop of ink. Most of all, since a worker measures viscosity of ink discontinuously and regulates it, the viscosity of ink cannot be maintained uniformly.

In addition, a method for measuring viscosity of ink by installing a mechanical measurement device is installed in the flow path of the ink has been proposed. However, in this case, the ink flow path of the measurement device is frequently clogged due to the ink having relatively greater viscosity, and also this method does not allow a worker to easily separate and clean the measurement device. Thus, a new measurement device should be frequently exchanged with an existing one, disadvantageously in terms of economy.

DISCLOSURE OF INVENTION

Technical Problem

The present invention is designed to solve the above problems of the prior art, and therefore it is an object of the invention to provide an apparatus for regulating viscosity of ink, which is installed on a flow path of ink to be always capable of measuring and regulating viscosity of ink.

Another object of the invention is to provide an apparatus for regulating viscosity of ink, which enables to measure an accurate viscosity of ink and also may allow a user to easily dissemble the apparatus and remove ink when a flow path is clogged due to the ink.

Technical Solution

In order to accomplish the above object, the present invention provides an apparatus for regulating viscosity of ink, which is installed on a flow path of ink in a printing device for regulation of ink viscosity, the apparatus including a housing installed on the flow path and having an introduction hole and a discharge hole through which ink is introduced and discharged; a rotary shaft installed in the housing and to which at least one rotating fan is coupled to rotate along with flow of the ink; a sensed member having a sensed body at one end thereof and coupled to the rotary shaft to rotate together with the rotary shaft; and a sensor for sensing the sensed body.

In addition, the apparatus for regulating viscosity of ink further includes a receptacle receiving the rotary shaft to be rotatable and detachably coupled in the housing, the receptacle having an inlet communicated with the introduction hole of the housing and an outlet communicated with the discharge hole of the housing.

Preferably, the receptacle is provided with at least one ink passage member in which a plurality of flow paths are uniformly formed for guiding the ink to flow linearly. More preferably, the rotating fan and the ink passage member are positioned alternately.

According to the present invention, an ink flow rate changing means for changing a flow rate of the ink depending on viscosity of the ink introduced into the receptacle and then discharged out of the receptacle is further provided.

Preferably, the ink flow rate changing means includes a first disk member coupled to the outlet of the receptacle and in which a plurality of ink passing holes are formed for the ink to pass therethrough; and a second disk member spaced apart from the first disk member by an ink flow gap and in which a plurality of ink discharge holes are formed for discharging the ink flowing through the ink passing holes.

As an alternative, the ink flow rate changing means includes a first disk member coupled to the outlet of the receptacle and having an opening through which the ink is capable of passing; and a second disk member having a plurality of micro holes through which the ink passing through the first disk member is discharged.

Preferably, the sensed member is exposed out of the receptacle.

The apparatus for regulating viscosity of ink according to the present invention may further include an ink pressure regulating means for keeping pressure of the ink introduced into the receptacle constantly.

Preferably, a space for the ink to flow is formed between an outer circumference of the receptacle and an inner circumference of the housing, and the ink pressure regulating means keeps pressure of the ink constantly by controlling a flow rate of the ink flowing through the space.

Preferably, the ink pressure regulating means includes an outflow hole through which the ink introduced through the space between the inner circumference of the housing and the outer circumference of the receptacle is discharged; and an elastic member for selectively opening and closing the outflow hole according to outflow pressure of the ink.

BRIEF DESCRIPTION OF THE DRAWINGS

FIG. 1 is a diagram showing one example for illustrating an ink viscosity measuring method according to the prior art;

FIG. 2 is a schematic view showing a printing device adopting an apparatus for regulating viscosity of ink according to a preferred embodiment of the present invention;

FIG. 3 is a schematic view showing an apparatus for regulating viscosity of ink according to the preferred embodiment of the present invention;

FIG. 4 is a bottom view showing a shaft support of the apparatus for regulating viscosity of ink according to the preferred embodiment of the present invention;

FIG. 5 is a perspective view schematically showing an ink passage member provided to the apparatus for regulating viscosity of ink according to the preferred embodiment of the present invention;

FIG. 6 is a partial perspective view schematically showing an inflow unit of a receptacle provided to the apparatus for regulating viscosity of ink according to the preferred embodiment of the present invention;

FIG. 7 is a plane view schematically showing a rotating fan provided to the apparatus for regulating viscosity of ink according to the preferred embodiment of the present invention;

FIGS. 8 and 9 are partially sectioned perspective views showing a first disk member provided to the apparatus for regulating viscosity of ink according to the preferred embodiment of the present invention, viewed from upper and lower positions respectively;

FIG. 10 is a partially sectioned perspective view showing a second disk member provided to the apparatus for regulating viscosity of ink according to the preferred embodiment of the present invention, viewed from a lower position;

FIG. 11 is a partially sectioned perspective view showing an ink pressure regulating means provided to the apparatus for regulating viscosity of ink according to the preferred embodiment of the present invention;

FIG. 12 is a schematic sectional view showing an apparatus for regulating viscosity of ink according to another embodiment of the present invention;

FIG. 13 is a bottom view showing a first disk adopted in the apparatus for regulating viscosity of ink according to another embodiment of the present invention; and FIG. 14 is a partially sectioned perspective view showing a second disk member adopted in the apparatus for regulating viscosity of ink according to another embodiment of the present invention.

BEST MODE FOR CARRYING OUT THE INVENTION

FIG. 2 is a schematic diagram showing a printing device adopting an apparatus for regulating viscosity of ink according to a preferred embodiment of the present invention.

Ink stored in a storage tank 10 is sent to a printing container 13 through a supply passage 12 by means of a driving force of a driving pump 11.

On the printing container 13, a printing roller 14 and a press roller 15 contacting with the printing roller 14 and rotating together with the printing roller 14 are installed.

An unprinted fabric 100 passes through the printing roller 14 and the press roller 15, and at this time the printing roller 14 gets wet with the ink contained in the printing container 13 to conduct a printing work. The ink in the printing container 13 returns to the storage tank 10 through a retrieving passage 16, thereby ensuring circulation. Reference numeral 17 denotes a stirrer for stirring the ink in the storage tank 10.

The ink viscosity regulating apparatus 200 according to the preferred embodiment of the present invention is installed on a flow path of ink. Preferably, an introduction hole 201 of the ink viscosity regulating apparatus 200 is connected to an introduction passage 19 communicated with the supply passage 12 so that ink is introduced through it, and a discharge hole 202 is connected to a discharge passage 20 toward the storage tank 10 so that ink is discharged through it.

In addition, an introduction pump 18 is installed to the introduction passage 19 so as to suck in ink and then supply the ink to the ink viscosity regulating apparatus 200.

The ink viscosity regulating apparatus 200 measures viscosity in ink, and makes solvent be additionally input if the viscosity of ink exceeds a standard value. That is to say, solvent 23 contained in a container 22 is input to the flow path of the ink by opening a solvent supply valve 21.

FIG. 3 is a sectional view schematically showing the apparatus for regulating viscosity of ink according to a preferred embodiment of the present invention.

Referring to FIG. 3, the ink viscosity regulating apparatus of the present invention includes a hosing 210 in which the introduction hole 201 connected to the introduction passage 19 and the discharge hole 202 connected to the discharge passage 20 are formed.

The housing 210 has a cylindrical shape so that the introduced ink may flow, and preferably its one end opposite to the introduction hole 201 is open so that inner components may be assembled and dissembled. Specifically, a cover 220 may be detachably coupled to the open end. Preferably, one end of the cover 220 is coupled to the housing 210 by means of a hinge 221, and the other end is provided with a latch 222 so as to be selectively fixed to the housing 210.

Preferably, the housing 210 is composed of a small diameter portion 211 having a cylindrical shape with a relatively smaller diameter, and a large diameter portion 212 extended from the small diameter portion 211 and having a cylindrical shape with a relatively larger diameter.

A receptacle 230 for receiving a rotary shaft 240 rotating along with the flow of ink that flows as mentioned below is coupled to the small diameter portion 211 of the housing 210. The receptacle 230 includes a cylindrical portion 231 received in the small diameter portion 211 of the housing 210, and an extension 232 extended outward from the cylindrical portion 231 toward the large diameter portion 212 of the housing 210 in a radial direction. Here, the cylindrical portion 231 is installed so that its outer circumference is spaced apart from the inner circumference of the small diameter portion 211 of the housing by a predetermined interval, thereby forming a space between the housing 210 and the small diameter portion 211 for the ink to be capable of flow. This space acts as a passage for regulating an introduction pressure of ink as described later.

A shaft support 233 supporting the rotary shaft 240 is installed to the cylindrical portion 231 of the receptacle 230. Referring to FIG. 4, a central through hole 233a is formed in the shaft support 233 so that the rotary shaft 240 passes through it, and also an opening 233b is also formed therein for the ink to flow. More preferably, the inner circumference of the central through hole 233a of the shaft support 233 is processed sharp to minimize an area contacting with the rotary shaft 240 so that a frictional resistance is minimized when the rotary shaft is rotating.

In addition, a plurality of ink passage members 235 in which a plurality of flow paths 235a with the same size are perforated in parallel are installed over the whole area in the cylindrical portion 231 of the receptacle 230 as shown in FIG. 5. The ink passage members 235 play a role of providing a path so that the ink flowing in the receptacle 230 may become linear, namely have a laminar flow. The ink passage members 235 are provided at regular intervals, and preferably provided alternately between the rotating fans coupled to the rotary shaft 240. In FIG. 5, reference numeral 235b designates a central through hole through which the rotary shaft 240 passes.

As shown in FIG. 6, a plurality of extension brackets 236 are extended from an inlet of the receptacle 230 in a length direction, and a shaft support bracket 237 is perpendicularly connected to an end of the extension brackets 236. The shaft support bracket 237 supports in contact with the end of the rotary shaft 240 received in the receptacle 230.

Preferably, a guide bracket 238 having a central through hole 238a for the rotary shaft 240 to pass through and supporting the rotary shaft 240 may be further provided between the extension brackets 236. More preferably, the inner circumference of the central through hole 238a of the guide bracket 238 is processed sharp to minimize an area contacting with the rotary shaft 240 so that a frictional resistance is minimized when the rotary shaft is rotating.

Though a detailed configuration for guiding and supporting the rotary shaft is illustrated in this embodiment, it should be understood that the present invention is not limited to the above and various existing configurations supporting the rotary shaft may be adopted.

According to the present invention, a rotating assembly is received in the receptacle 230, which includes the rotary shaft 240, and at least one rotating fan 250 coupled to the rotary shaft 240.

The rotary shaft 240 is rotatably coupled through the central through hole 233a of the shaft support 233 and the central through hole 235b of the ink passage member 235 provided to the receptacle 230. One end 241 of the rotary shaft 240 is supported in contact with the shaft support bracket 237 described above, and the other end is supported in contact with an ink flow rate changing means coupled to the extension 232 of the receptacle 230. Preferably, both ends of the rotary shaft 240 contacting with the shaft support bracket 237 and the ink flow rate changing means are processed sharp to minimize a frictional resistance.

At least one rotating fan 250 is coupled to the rotary shaft 240, as shown in FIG. 7. Referring to FIG. 7, the rotating fan 250 includes a plurality of fans 251 extended in radial direction, and a rim 252 connecting ends of the fans 251. An opening 250a is formed between the fans 251 so that the ink may flow through it. Size and number of the fan may be suitably designed in consideration of ink viscosity and measurement range.

According to the present invention, the rotating fan 250 is preferably installed between the ink passage members 235 in the receptacle 230. That is to say, the rotating fan 250 and the ink passage member 235 are provided alternately. In this connection, though flow of the ink passing through the rotating fan 250 is distorted or becomes turbulent, it may be changed into a uniform laminar flow with passing through the subsequent ink passage member 235, so viscosity may be measured for ink having stable flow.

In addition, as shown in FIG. 6, a sensed member 260 is coupled to the rotary shaft 240 to rotate together with the rotary shaft 240. The sensed member 260 includes a plurality of branches 261 coupled to the rotary shaft 240, and a sensed body 262 is coupled to each branch 261 for the measurement of rotational frequency of the rotary shaft. The sensed body 262 may be magnet or steel, and magnet is preferred. As an alternative, the sensed member 260 may be prepared integrally using plastic magnet that has magnetism.

Preferably, the sensed member 260 is designed to minimize a frictional force with the ink while rotating, and it should be understood that its shape and structure and number of the branches may be variously changed for this purpose.

In addition, a sensor 270 for sensing the sensed body 262 installed to the sensed member 260 is installed to an outer side of the housing 210. According to a preferred embodiment of the present invention, when the sensed member 260 rotates, the sensor 270 senses the sensed body 262 to measure the rotational frequency of the rotary shaft. In case the sensed body 262 is magnet, change of a magnetic field will be sensed.

According to the present invention, the ink flow rate changing means is installed to an outlet of the receptacle 230 so that speed of the ink introduced into and discharged out of the receptacle 230 is changed depending on viscosity. Specifically, the ink flow rate changing means includes a first disk member 290 and a second disk member 300.

As shown in FIGS. 8 and 9, the first disk member 290 is detachably coupled to a circumference 230b of the outlet of the receptacle 230, namely at the end of the extension 232, and a plurality of ink passing holes 290a are formed therein so that the ink may pass through them. Preferably, a first circular groove 291 is formed on the upper surface of the first disk member 290, and a plurality of ink passing holes 290a are formed in the first groove 291.

In addition, the second disk member 300 is coupled to have a space with regard to the first disk member 290 as much as 'an ink flow gap' and a plurality of ink discharge holes 300a are formed therein so that the ink flowing through the ink passing holes 290a of the first disk member 290 may be discharged, as shown in FIG. 10. Preferably, a second groove 301 is formed in the lower surface of the second disk member 300 along a concentric circle with a diameter different from the first groove 291 formed in the first disk member 290, and a plurality of ink discharge holes 300a are formed in the second groove 301. The first and second grooves 291, 301 give a buffering space where the ink discharged through the ink discharge holes 300a and the ink passing through the ink flow gap are gathered and stay. More preferably, a buffering groove 304 may be further formed in the lower surface of the second disk member 300 facing with the ink passing holes 290a of the first disk member 290 so that the ink flowing through the ink passing holes 290a may stay there.

According to the present invention, a space protrusion 292 is formed on the upper surface of the first disk member 290, and a space groove 302 is formed in the lower surface of the second disk member 300 so that the space protrusion 292 may be coupled thereto. As an alternative, the space protrusion and the space groove may be exchanged. In addition, it is also possible that a space protrusion 230c is formed on the receptacle 230, and a space groove 300b is formed in the second disk member 300 correspondingly. The space protrusion and the space groove keep a gap between the first and second disk members 290, 300, arranges coupling positions of the receptacle 230 and the disk members 290, 300, and also separates a flow path of the ink for measurement of viscosity and a flow path of the ink for control of introduction pressure.

The first and second disk members 290, 300 are arranged with each other when the space protrusion 292 and the space groove 302 are coupled to each other. At this time, the upper surface of the first disk member 290 and the lower surface of the second disk member 300 are spaced apart from each other as much as the 'ink flow gap' where the ink may flow.

The term ink flow gap' used in this specification and the appended claims is corresponding to a gap between the first disk member 290 and the second disk member 300, which plays a role of changing a flow rate depending on viscosity of the ink. That is to say, if viscosity of the ink flowing through a constant ink flow gap is high, the flow rate will be relatively slow, while, if the viscosity of the ink is low, the flow rate will be relatively fast. This ink flow gap is not fixed to a specific value, but it may be suitably set depending on kind and viscosity of ink or capacity of a printing device. Thus, though the ink flow gap is not set to a specific value, those skilled in the art may sufficiently understand the above meaning and apply it based on the above, so it will not be interpreted as an unclear word.

The ink introduced into the receptacle 230 is flowed out through the ink passing hole 290a of the first disk member 290, flows between the upper surface of the first disk member 290 and the lower surface of the second disk member 300, spaced apart as much as the 'ink flow gap' and then is discharged through the ink discharge hole 300a of the second disk member 300.

Preferably, a central shaft 293 is extended at the center of the first disk member 290, and a support 303 having a hollow 303a in which the central shaft 293 is inserted and supported is formed at the center of the second disk member 300. In addition, the support 303 is elastically biased by an elastic means 310, so the first and second disk members 290, 300 are pressed toward the receptacle 230. Preferably, the elastic means 310 may include a press member 311 corresponding to its shape so as to give a stable elastic force.

According to the present invention, the first and second disk members 290, 300 are all detachably coupled to the receptacle 230 so as to be easily separated for cleaning or managing the interior of the receptacle 230.

The ink viscosity regulating apparatus of the present invention includes an ink pressure regulating means for keeping an introduction pressure of ink by bypassing the ink in case the ink introduced into the receptacle 230 has excessive pressure.

The ink pressure regulating means includes an elastic member 330 installed to an outflow hole 320 through which the ink introduced through a space between the inner circumference of the housing 210 and the outer circumference of the receptacle 230 is discharged to selectively open or close the outflow hole 320 by means of elasticity, as shown in FIG. 3.

More specifically, referring to FIGS. 3, 10 and 11, a path for ink to flow is formed between the inner circumference of the housing 210 and the outer circumference of the receptacle 230, and this path is communicated with a plurality of outflow holes 320 formed the outline of the second disk member 300 coupled to the outlet of the receptacle 230.

A seat 321 is prepared in the outflow hole 320, and it is coupled by fitting of a cylindrical coupling member 340 after the elastic member 330 is placed thereon. The elastic member 330 is made of metal material such as steel or plastic material with excellent elasticity, and a plurality of slits 331 are formed therein to ensure elastic deformation.

Thus, in case the pressure of ink discharged through the outflow hole 320 is low, only a small amount of ink will be flowed out through the slits 331 formed in the elastic member 330. On the other hand, in case the pressure of oil flowing out through the outflow hole 320 is high, the elastic member 330 around the slits 331 is bent to expand an outflow space of ink further so that a more amount of ink is flowed out. As a result, the pressure of ink may be suitably regulated by means of elastic resistance of the elastic member 330.

Though it has been illustrated that the outflow hole and the elastic member are provided to the second disk member, the present invention is not described to the above. That is to say, the outflow hole and/or the elastic member may be selectively provided to any of the first and second disk members and the circumference of the receptacle, and it may also be installed separately.

Furthermore, the ink pressure regulating means is not limited to this embodiment, but various check valves that closes the outflow hole in case the pressure of ink flowing out through the outflow hole is smaller than a standard value, and opens the outflow hole in case the pressure of ink is greater than a standard value may be applied.

Now, operation of the ink viscosity regulating apparatus according to the preferred embodiment of the present invention as mentioned above will be described.

During the operation of the printing device shown in FIG. 2, the ink viscosity regulating apparatus 200 of the present invention measures viscosity of the ink in real time. More specifically, the ink flowing by operation of the introduction pump 18 is introduced into the housing 210 of the ink viscosity regulating apparatus 200 through the introduction passage 19.

The ink introduced into the housing 210 flows into the receptacle 230 as shown by arrow in FIG. 3, and at the same time a part of the ink flows along the space formed between the inner circumference of the housing 210 and the outer circumference of the receptacle 230.

At this time, in case the pressure of the introduced ink exceeds a predetermined range, a flow rate of the ink is regulated by means of operation of the elastic member 330 prepared to the outflow hole 320 as mentioned above.

Meanwhile, the ink introduced into the cylindrical portion 231 of the receptacle 230 reaches the rotating fan 250, and thus the rotating fan 250 rotates on the rotary shaft 240.

The ink passing through the rotating fan 250 passes through the flow path 235a of the ink passage member 255 again to make its flow linear, and the ink discharged from the flow path 235a is collided with the rotating fan 250 again to rotate the rotating fan. At this time, air bubbles may be absorbed to the ink passage member 235 or the like while the ink is flowing, but such absorption of air bubbles may be eliminated by means of rotation of the rotating fan 250.

The ink passing through the receptacle 230 passes through the ink passing hole 290a of the first disk member 290 to fill the first groove 291 and/or the buffering groove 304. Subsequently, the ink passes between the first disk member 290 and the second disk member 300, spaced apart as much as the ink flow gap, and then reaches the second groove 301 formed in the lower surface of the second disk member 300. After that, the ink flows through a plurality of ink discharge holes 300a formed in the second groove 301 and then is discharged through the discharge passage 20.

During the above procedure, the rotary shaft 240 is rotated by means of the flow of ink, and at this time the sensed member 260 coupled to the rotary shaft 240 is also rotated at the same speed as the rotating fan. Then, the sensor 270 senses the sensed body 262 mounted to the sensed member 260 to measure the rotational frequency. If the rotational frequency is measured, the viscosity of ink may be calculated according to formulas of the hydraulic engineering. For example, if the viscosity of ink is increased, a flow rate of the ink passing through the ink flow gap between the first and second disk members 290, 300 is decreased, accordingly reducing a rotational frequency of the rotary shaft. Such a calculating method is a well-known theory in the art, and not described here in detail.

If the viscosity of ink exceeds a predetermined range as a result of the measurement, this signal is sent to a controller, not shown, and then the controller opens the solvent supply valve 21 to put the solvent 23 contained in the container 22 to a flow path of the ink so that viscosity may be kept suitably.

As mentioned above, the ink viscosity regulating apparatus of the present invention may measures and correct viscosity of ink in real time.

The ink viscosity regulating apparatus of the present invention gives excellent effects even in terms of cleaning and maintenance. That is to say, in case of cleaning or washing is needed due to adherence of ink in the regulating apparatus, the apparatus may be conveniently opened with opening the cover 220. After that, the first and second disk members 290, 300 are taken out of the housing, and then the receptacle 230 may be wholly taken out so as to facilitate easy cleaning, repair and exchange of parts. In addition, since the sensed member 260 is exposed, it may be very easily cleaned using a solvent. Such features of the present invention is helpful for easing cleaning and maintenance of the ink viscosity regulating apparatus and also enables to use the apparatus permanently.

FIG. 12 shows an ink viscosity regulating apparatus provided with an ink flow rate changing means according to another embodiment of the present invention. Here, the same reference numeral as in the former drawings designates the same component.

In this embodiment, a first disk member 290' includes a plurality of spokes 290b' between which an opening 290a' for ink to pass is formed, and a rim 290c' connecting ends of the spokes 290b'.

A second disk member 300' coupled to the upper surface of the first disk member 290' has a plurality of micro holes 300a' for discharging the ink in the receptacle 230. In addition, an ink pressure regulating means is also provided to the second disk member 300' as in the former embodiment.

In this embodiment, the ink flow rate changing means is the micro holes 300a' formed in the second disk member 300'. That is to say, if the viscosity of flowing ink is high, a flow rate of the ink passing through the micro holes 300a' will be decreased. The micro holes 300a' may be suitably set depending on kind and viscosity of used ink and capacity of the printing device.

In this embodiment, all operations except for the difference in the ink flow rate changing means are identical to those of the former embodiment, and not described in detail here.

INDUSTRIAL APPLICABILITY

According to the ink viscosity regulating apparatus of the present invention, viscosity of ink circulating in a flow path of the ink is measured during the printing work, enabling successive measurement in real time. In addition, since the viscosity of ink is accordingly corrected instantly, quality of printing is improved and life of the printing device may be extended.

Moreover, the ink viscosity regulating apparatus of the present invention is designed to ensure easy assembling and dissembling, allowing convenient cleaning and maintenance and also enabling to use the apparatus permanently.

The present invention has been described in detail. However, it should be understood that the detailed description and specific examples, while indicating preferred embodiments of the invention, are given by way of illustration only, since various changes and modifications within the spirit and scope of the invention will become apparent to those skilled in the art from this detailed description.

The invention claimed is:

1. An apparatus for regulating viscosity of ink, which is installed on a flow path of ink in a printing device, the apparatus comprising:
  a housing installed on the flow path, having an introduction hole and a discharge hole, through which ink is respectively introduced and discharged;
  a rotary shaft installed in the housing, to which at least one rotating fan is coupled to rotate along with flow of the ink;
  a sensed member having a sensed body at one end thereof, coupled to the rotary shaft to rotate together with the rotary shaft;
  a sensor to sense the sensed body;
  a receptacle to receive the rotary shaft so as to be rotatable and detachably coupled in the housing, the receptacle having an inlet communicating with the introduction hole of the housing, and an outlet communicating with the discharge hole of the housing; and
  an ink flow rate changing means to change the flow rate of the ink, depending on the viscosity of the ink introduced into the receptacle, comprising:
    a first disk member coupled to the outlet of the receptacle, in which a plurality of ink passing holes are formed in a first groove formed on the first disk member in a circular shape, for the ink to pass through; and
    a second disk member spaced apart from the first disk member by an ink flow gap, in which a plurality of ink discharge holes are formed in a second groove formed on the second disk member, along a concentric circle having a different diameter from the first groove, to discharge the ink flowing through the ink passing holes.

2. An apparatus for regulating viscosity of ink, which is installed on a flow path of ink in a printing device, the apparatus comprising:
  a housing installed on the flow path, having an introduction hole and a discharge hole, through which ink is respectively introduced and discharged;
  a rotary shaft installed in the housing, to which at least one rotating fan is coupled to rotate along with flow of the ink;
  a sensed member having a sensed body at one end thereof, coupled to the rotary shaft to rotate together with the rotary shaft;
  a sensor to sense the sensed body;
  a receptacle to receive the rotary shaft so as to be rotatable and detachably coupled in the housing, the receptacle having an inlet communicating with the introduction hole of the housing, and an outlet communicating with the discharge hole of the housing; and
  an ink flow rate changing means to change the flow rate of the ink, depending on the viscosity of the ink introduced into the receptacle, comprising:
    a first disk member coupled to the outlet of the receptacle, in which a plurality of ink passing holes are formed for the ink to pass through; and
    a second disk member spaced apart from the first disk member by an ink flow gap, in which a plurality of ink discharge holes are formed to discharge the ink flowing through the ink passing holes,
  wherein a space protrusion is formed on one of the first and second disk members and a space groove is formed in the other of the first and second disk members, so as to be coupled with the space protrusion, whereby an ink flow gap is set between the first and second disk members, by the coupling of the space protrusion and the space groove.

3. An apparatus for regulating viscosity of ink, which is installed on a flow path of ink in a printing device, the apparatus comprising:
  a housing installed on the flow path, having an introduction hole and a discharge hole, through which ink is respectively introduced and discharged;
  a rotary shaft installed in the housing, to which at least one rotating fan is coupled to rotate along with flow of the ink;
  a sensed member having a sensed body at one end thereof, coupled to the rotary shaft to rotate together with the rotary shaft;
  a sensor to sense the sensed body;
  a receptacle to receive the rotary shaft so as to be rotatable and detachably coupled in the housing, the receptacle having an inlet communicating with the introduction hole of the housing, and an outlet communicating with the discharge hole of the housing; and an ink flow rate changing means to change a flow rate of the ink, depending on the viscosity of the ink introduced into the receptacle, comprising:
- a first disk member coupled to the outlet of the receptacle, having an opening through which the ink passes; and
- a second disk member having a plurality of micro holes through which the ink passing through the first disk member is discharged, wherein a space protrusion is formed on one of the first and second disk members and a space groove is formed in the other of the first and second disk members, so as to be coupled with the space protrusion, whereby a gap is set between the first and second disk members by the coupling of the space protrusion and the space groove.

4. An apparatus for regulating viscosity of ink, which is installed on a flow path of ink in a printing device, the apparatus comprising:
- a housing installed on the flow path, having an introduction hole and a discharge hole, through which ink is respectively introduced and discharged;
- a rotary shaft installed in the housing, to which at least one rotating fan is coupled to rotate along with flow of the ink;
- a sensed member having a sensed body at one end thereof, coupled to the rotary shaft to rotate together with the rotary shaft;
- a sensor to sense the sensed body;
- a receptacle to receive the rotary shaft so as to be rotatable and detachably coupled in the housing, the receptacle having an inlet communicating with the introduction hole of the housing, and an outlet communicating with the discharge hole of the housing;
- an ink pressure regulating means to keep pressure of the ink introduced into the receptacle constant, wherein,
- a space for the ink to flow is formed between the outer circumference of the receptacle and the inner circumference of the housing,
- the ink pressure regulating means keeps pressure of the ink constant, by controlling a flow rate of the ink through the space, and
- the ink pressure regulating means includes:
  - an outflow hole through which the ink introduced through the space between the inner circumference of the housing and the outer circumference of the receptacle is discharged; and
  - an elastic member to selectively open and close the outflow hole according to outflow pressure of the ink.

* * * * *